United States Patent [19]

Schachar

[11] Patent Number: 4,907,585

[45] Date of Patent: Mar. 13, 1990

[54] METHOD FOR IMPROVING FARSIGHTEDNESS

[76] Inventor: Ronald A. Schachar, P.O. Box 1039, Denison, Tex. 75020

[21] Appl. No.: 128,431

[22] Filed: Dec. 3, 1987

[51] Int. Cl.$^4$ .............................................. A61B 17/36
[52] U.S. Cl. ...................................... 606/28; 128/399
[58] Field of Search ...................... 128/303.1, 395, 400

[56] References Cited

U.S. PATENT DOCUMENTS

| 4,326,529 | 4/1982 | Doss et al. | 128/303.1 |
| 4,381,007 | 4/1983 | Doss | 128/303.1 |
| 4,461,294 | 7/1984 | Baron | 128/303.1 |
| 4,564,011 | 1/1986 | Goldman | 128/303.1 |
| 4,682,597 | 7/1987 | Myers | 604/22 |

FOREIGN PATENT DOCUMENTS

| 3315303 | 11/1984 | Fed. Rep. of Germany | 128/303.1 |
| 831119 | 5/1981 | U.S.S.R. | 128/303.1 |

OTHER PUBLICATIONS

"Corneal Surgery Vol. II" by L. Gerard; The C. V. Mosby Co., St. Louis, Toronto, London 1981.
"Thermokeratoplasty (TKP) Temperature Profile" by Shaw et al, Invest. Ophthal, vol. 13, No. 3, 3/74, pp 181–186.
"Thermokeratoplasty in the Treatment of Keratoconus" by Gosset et al, Am. J. Ophthal; vol. 79, No. 2, Feb. 1975, pp. 226–232.

*Primary Examiner*—Lee S. Cohen
*Assistant Examiner*—David Shay
*Attorney, Agent, or Firm*—Baker, Mills & Glast

[57] ABSTRACT

The specification discloses apparatus for changing the radius of curvature of a cornea, which includes a needle (34) for being inserted into the periphery (14) of the cornea (10). A device (36, 38, 40) heats the needle (34) to a temperature sufficient to degrade a plurality of elongated regions (12) of the corneal stroma, such that the limbus of the cornea is constricted to change the radius of curvature of the cornea.

7 Claims, 1 Drawing Sheet

METHOD FOR IMPROVING FARSIGHTEDNESS

TECHNICAL FIELD OF THE INVENTION

The present invention relates to treatment of the human cornea, and more particularly relates to an apparatus and method for improving farsightedness of the human eye by constricting the limbal ring of the human cornea.

BACKGROUND OF THE INVENTION

It has been heretofore known to perform operations upon the eye in order to improve nearsightedness. Specifically, a technique known as radial keratotomy has been known wherein radial slits are made upon the exterior of the cornea in order to change the shape of the cornea to improve nearsightedness.

It has recently been proposed to perform operations upon the eye to improve farsightedness by making selected thermal burn spots upon the exterior periphery of the cornea. In this way, the limbal ring of the cornea is effectively constricted or the circumference thereof is reduced in order to change the shape of the cornea in order to improve farsightedness. Such burn spots have been made by heated needles and attempts have also been made to utilize laser beams. However, such efforts have not been totally satisfactory, and the correction has tended not to be long lasting. This is believed to be because the heat generated by the heated needle or the laser beam is diffused or disseminated throughout the surface epithelium of the cornea and does not permanently degrade the stroma. Thus, a need has arisen for a technique for permanently degrading selected areas of the corneal stroma in order to tighten or reduce the circumference of the limbal ring in order to provide the desired correction to the eye.

SUMMARY OF THE INVENTION

The present invention describes a method and apparatus for improving farsighted vision in the human eye which substantially eliminates or reduces difficulties in previous attempts. Specifically, in accordance with one aspect of the invention, a method of improving farsighted vision in the human eye includes heating elongated areas of the collagen tissue in the stroma of the cornea of the eye to a sufficient level to permanently degrade the collagen in the elongated areas. The permanently degraded elongated areas act to constrict the circumference of the limbal ring of the cornea to change the shape of the cornea. In the preferred embodiment of the invention, a needle is inserted through the peripheral areas of the cornea into the stroma and the needle is heated in order to degrade the stroma collagens to the desired extent.

In accordance with another aspect of the invention, a method of changing the radius of curvature of the cornea includes inserting an elongated member into the periphery of the cornea. The elongated member is then heated to a temperature sufficient to degrade a plurality of elongated regions of corneal stroma, such that the limbus of the cornea is constricted to change the radius of curvature of the cornea.

In another aspect of the invention, apparatus is provided to improve farsighted vision in the human eye which includes an elongated needle which may be inserted into the cornea of the eye. Apparatus is provided to heat the needle to heat elongated areas of the collagen of the cornea of the eye to a sufficient temperature to degrade the collagen in the elongated areas. The degraded elongated areas act to constrict the circumference of the limbus of the cornea to change the shape of the cornea.

DESCRIPTION OF THE PREFERRED EMBODIMENT

For a more complete understanding of the present invention and for further advantages thereof, reference is now made to the following detailed description taken in conjunction with the accompanying drawing, in which.

DETAILED DESCRIPTION WITH REFERENCE TO THE DRAWINGS

Figure 1:
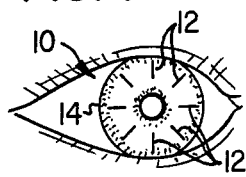
FIG. 1 is a front view of a human cornea illustrating the aftereffects of the present technique.

FIG. 1 illustrates a front view of a human cornea, generally identified by the numeral 10. Cornea 10 has been altered in accordance with the present invention in order to reduce the effects of farsightedness. In accordance with the invention, a series of radially extending spoke-like burn or thermally degraded areas 12 have been formed within the stroma of the cornea. Although the front view of the human eye shown in FIG. 1 appears to show the spoke-like burns 12 on the exterior surface of the cornea 10, it will be understood that the burn areas 12 are solely within the stroma and will normally be visible from the front of the human eye as barely discernable hazes.

In accordance with the invention, the burns 12 are symmetrically spaced about the outer periphery of the cornea in order to tighten or constrict the cornea limbus 14. This tightening of the limbus 14 causes the shape of the cornea 10 to be changed such that the curvature thereof is increased. This change in curvature tends to reduce and even cure farsightedness in the normal human eye. The number of burns 12 and the length thereof can be varied in order to change the curvature of the cornea 10 in order to selectively cure individual eyes.

Figure 2:
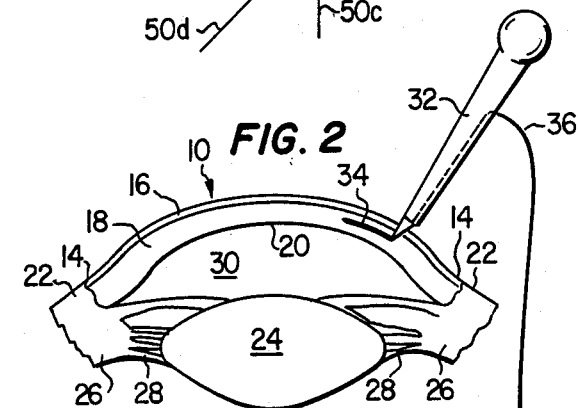
FIG. 2 is a cross sectional view of the human cornea illustrating the preferred embodiment of the present technique.

FIG. 2 illustrates in detail the formation of the burns 12. FIG. 2 illustrates a cross sectional view of a human cornea and illustrates the stroma 18, which separates the epithelium 16 from Descenet's membrane 20. As is known, the cornea 10 is connected at the limbus or limbal ring 14 to the schlera 22. The lens 24 is connected to the ciliary body 26 by ligaments 28. The cornea 10 and the lens 24 are separated by the anterior chamber 30.

Referring to FIG. 2, the present invention utilizes a handle 32 of sufficient size to be grasped by the surgeon and having at its lower end a needle 34. Needle 34 is electrically and thermally insulated from the handle. An electrical wire 36 extends from the handle 32 into contact with the needle 34 in order to carry electrical current to a resistive heating element in the needle 34. Electrical wire 36 extends through a switch 38 to an electrical power supply 40. In operation of the device shown in FIG. 2, the needle 34 is inserted into the stroma 18 by way of a conventional conjuctive flap operation or by being extended through the limbus 14. The needle 34 may be provided with a small radius of curvature essentially equal to that of the cornea, or approximately 8 millimeters radius of curvature, in order that the needle 34 does not extend through the epithelium or through the Descenet's membrane or endothelium.

Once positioned, the switch 38 is moved to the on position, and electrical power is applied to the resistive heating element in needle 34. This causes the needle 34 to become heated to over 60 degrees Centigrade in order that protein in the stroma is degenerated to provide the designed burn 12. The switch 38 is then opened, and the needle is withdrawn. The needle 34 may then be placed in another position along the radius of the cornea and the switch 38 again energized in order to make another burn 12. The operation of this continues until all desired burn areas 12 are placed in order to enhance the sight of the cornea.

Figure 3:
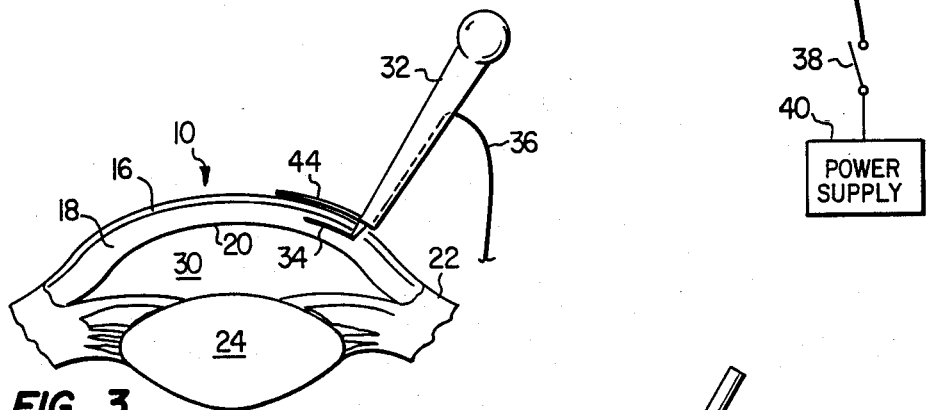
FIG. 3 is a side view of a human cornea illustrating the use of an improved embodiment of the invention.

It will be seen that it is important that the needle 34 not extend through the epithelium or through the endothelium. FIG. 3 illustrates a variant of the invention wherein a guard 44 is attached to the handle 32. The guard 44 extends generally parallel above the needle 34 and at essentially the same radius of curvature as the cornea. In this way, the guard 44 may be visually sighted to lay along the outer surface of the cornea 10 in order that the needle 34 be very accurately placed within the stroma 18. The use of the guide 34 thus prevents injury to the eye by assuring proper placement of the needle 34 during the operation. It will be understood that other guides may also be utilized with the present invention, such as a large guide which directly conforms to the exterior of the cornea in order to insure the proper placement of the needle 34.

Figure 4:
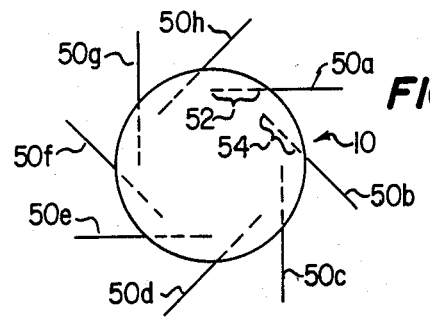
FIG. 4 is a front view of a human cornea illustrating an alternative embodiment of the present invention.

FIG. 4 illustrates another embodiment of the present invention, wherein needles constructed in accordance with the present invention are inserted generally tangentially around the limbus of the cornea. As may be seen, FIG. 4 illustrates eight positions 50a–h of a needle in accordance with the present invention. In this embodiment, the needle is inserted through the limbal ring 14 of the cornea 10 initially in the position shown as 50a. The dotted portion of 50a illustrates the position of the needle within the stroma of the cornea 10. Electrical current is then passed into the needle such that a burn area illustrated as 52 will be formed along the limbal ring of the cornea. The needle is then withdrawn and reinserted in position 50b. Current is then applied to the needle in order to form a second burn area 54 in the stroma. The process is then continued until eight burn areas oriented generally circumferentially about the limbal ring of the cornea are provided. In this way, farsightedness of the cornea 10 is essentially reduced.

Figure 5:
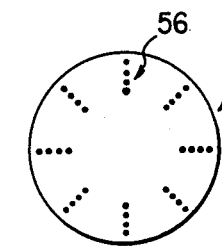
FIG. 5 is a front view of a human cornea illustrating yet another embodiment of the invention.
Figure 6:
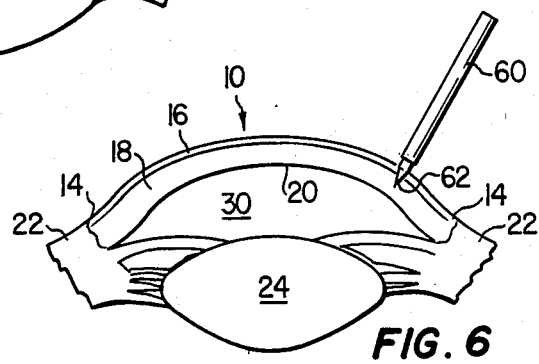
FIG. 6 is a sectional view of a human cornea illustrating yet another embodiment of the present invention.

FIGS. 5 and 6 illustrate yet another embodiment of the present invention, wherein burn dots are provided about the limbal ring of the cornea 10. As show in FIG. 5, instead of the elongated burn regions as shown in FIGS. 1–4, this embodiment of the invention utilizes linear series of dots 56 presented at eight or more locations about the limbal ring in order to provide the desired results. As shown in FIG. 6, these dots are formed by a needle 60 which is inserted through the exterior of the limbal ring 14 of the cornea. An important aspect of the present invention is that the needle 60 is electrically and thermally insulated from the tip 62. Tip 62 is very sharp in order to enable clean entry through the epithelium 16. Tip 62 is formed of a conductive resistive material such that when electricity is applied, the conductive material heats up. Tip 62 is thermally insulated from body 60 of the needle such that only the tip portion 62 is heated. In this way, heat is not dissipated within the epithelium, but is applied directly to the stroma 18. In this way, the effects of the operation are thought to be longer lasting and more effective than if the exterior portion of the cornea is heated.

In operation, the needle 60 is pushed through the epithelium into the stroma 18 and then electricity is applied to heat the needle tip 62 only. The needle is then withdrawn and reinserted at another desired location. This technique is not believed to be as effective as the technique shown in FIGS. 1-4 because of difficulty in accurately positioning the depth of the needle and because heat is not as effectively applied over a larger area in order to provide the improved results as shown by the technique of FIGS. 1-4.

Other variations, departures and modifications lying within the spirit of the invention and scope as defined by the appended claims will be obvious to those skilled in the art.

What is claimed is:

1. A method of changing the radius of curvature of a cornea comprising:
   inserting an elongated member into a plurality of locations about the periphery of the cornea, and
   heating said elongated member to a temperature sufficient to degrade a plurality of elongate regions of corneal stroma, such that the limbus of the cornea is constricted to change the radius of curvature of the cornea.

2. The method of claim 1 wherein said elongated member is inserted generally along radial lines of the cornea.

3. The method of claim 1 wherein said elongated member is inserted generally tangentially to the periphery of the cornea.

4. A method of changing the radius of curvature of a cornea comprising:
   inserting the end of an elongated member into a plurality of locations about the outer periphery of the cornea, and
   applying heat in a localized position of said end in order to raise the temperature only of the adjacent cornea stroma sufficiently to degrade the stroma.

5. A method of improving farsighted vision in the human eye, comprising the steps of:
   inserting a needle into peripheral areas of the cornea of the eye;
   heating said needle;
   degrading elongate areas of the collagen in the stroma of the cornea of the eye in response to said step of heating; and
   said degraded elongate areas acting to constrict the circumference of the limbal ring of the cornea to change the shape of the cornea.

6. The method of claim 5 wherein said elongate areas are disposed in said limbal ring area along radial lines of the cornea.

7. The method of claim 5 wherein said step of heating comprises:
   applying electrical current to said needle to generate heat therein.

* * * * *